United States Patent
Iyo et al.

(10) Patent No.: US 7,754,434 B2
(45) Date of Patent: Jul. 13, 2010

(54) DIAGNOSTIC AND EXAMINATION METHOD FOR EATING DISORDER

(75) Inventors: Masaomi Iyo, 21-15, Makuharihongo 7-chome, Hanamigawa-ku, Chiba-shi, Chiba 262-0033 (JP); Kenji Hashimoto, Nishitokyo (JP); Michiko Nakazato, Narashino (JP); Eiji Shimizu, Chiba (JP); Hiroki Koizumi, Chiba (JP)

(73) Assignee: Masaomi Iyo, Chiba-shi (JP)

( * ) Notice: Subject to any disclaimer, the term of this patent is extended or adjusted under 35 U.S.C. 154(b) by 1009 days.

(21) Appl. No.: 10/528,814

(22) PCT Filed: Sep. 24, 2003

(86) PCT No.: PCT/JP03/12134

§ 371 (c)(1),
(2), (4) Date: Apr. 19, 2005

(87) PCT Pub. No.: WO2004/029624

PCT Pub. Date: Apr. 8, 2004

(65) Prior Publication Data

US 2005/0244903 A1 Nov. 3, 2005

(51) Int. Cl.
*G01N 33/74* (2006.01)
*G01N 33/58* (2006.01)
*G01N 33/543* (2006.01)

(52) U.S. Cl. .................. 435/7.1; 435/7.7; 435/7.92

(58) Field of Classification Search .............. None
See application file for complete search history.

(56) References Cited

U.S. PATENT DOCUMENTS

2003/0149994 A1 8/2003 Heinrich et al.

FOREIGN PATENT DOCUMENTS

| JP | 8-501313 | 2/1996 |
| WO | WO 94/06455 | 3/1994 |
| WO | 94/23736 | 10/1994 |
| WO | WO 98/21245 | 5/1998 |
| WO | WO 03/011395 A2 | 2/2003 |
| WO | WO 2004/056385 A2 | 7/2004 |

OTHER PUBLICATIONS

Steven G. Kernie, et al., "BDNF regulates eating behavior and locomotor activity in mice", The EMBO Journal, XP002330841, vol. 19, No. 6, Mar. 2000, pp. 1290-1300.
Maribel Rios, et al., "Conditional Deletion of Brain-Derived Neurotrophic Factor in the Postnatal Brain Leads to Obesity and Hyperactivity", XP002455825, vol. 15, No. 10, Oct. 2001, pp. 1748-1757.
Ribases, M. et al. "Met66 in the bran-derived neurotrophic factor (BDNF) precursor is associated with anorexia nervosa restrictive type", Molecular Psychiatry, vol. 8, pp. 745-751 2003.
Ribases, M. et al. "Val66Met in the Brain Derived Neurotrophic Factor (BDNF) Precursor is associated with anorexia nervosa restrictive type", American Journal of Medical Genetics, vol. 114, No. 7, p. 739, O71 2002.
Nakazato, Michiko et al. "Decreased Levels of Serum Brain-Derived Neurotrophic Factor in Female Patients with Eating Disorders", Biol. Psychiatry, vol. 54, pp. 485-490 2003.
Masand, Prakash S. et al. "Selective Serotonin-Reuptake Inhibitors: An Update", Harv. Rev. Psychiatry, vol. 7, No. 2, pp. 69-84 1999.
Kaye, Walter et al. "Serotonin Neuronal Function and Selective Serotonin Reuptake Inhibitor Treatment in Anorexia and Bulimia Nervosa", Biol. Psychiatry, vol. 44, pp. 825-838 1998.
Lyons, W. Ernest et al. "Brain-derived neurotrophic factor-deficient mice develop aggressiveness and hyperphagia in conjunction with brain serotonergic abnormalities", PNAS, vol. 96, No. 26, pp. 15239-15244 1999.
Pelleymounter, M.A., et al, "Characteristics of BDNF-Induced Weight Loss", , Exprimental Neurology, 1995, vol. 131, No. 2, pp. 229-238.

*Primary Examiner*—Robert C Hayes
(74) *Attorney, Agent, or Firm*—Oblon, Spivak, McClelland, Maier & Neustadt, L.L.P.

(57) ABSTRACT

The present invention provides a diagnostic agent for eating disorders comprising as an active ingredient an antibody against brain-derived neurotrophic factor, and a method for detecting eating disorders comprising measuring of the concentration of a brain-derived neurotrophic factor in blood. Particularly, the eating disorders can easily be diagnosed by measuring the concentration of a brain-derived neurotrophic factor in blood of the patients with an antibody against brain-derived neurotrophic factor and a labeled antibody against brain-derived neurotrophic factor.

9 Claims, 5 Drawing Sheets

DIAGNOSTIC AND EXAMINATION METHOD FOR EATING DISORDER

TECHNICAL FIELD

The present invention relates to a diagnostic for eating disorders, and a method for examining eating disorders. More particularly, the present invention relates to a diagnostic for eating disorders, which comprises as the main ingredient an antibody against a brain-derived neurotrophic factor, a method for detecting eating disorders, which comprises measuring the concentration of the brain-derived neurotrophic factor in blood, a method for detecting an agent for treatment of eating disorders, which comprises measuring the concentration of the brain-derived neurotrophic factor in blood, and an agent for treatment of eating disorders, which comprises a compound increasing the brain-derived neurotrophic factor.

BACKGROUND ART

Anorexia nervosa (AN) and bulimia nervosa (BN) are eating disorders, from which 0.5 to 3.7% and 1.1-4.2% of female are suffered respectively over their lifetimes. It is said that the prevalence rate of eating disorders in male is about 10% of that in female. A majority of patients with eating disorders are female in puberty/adolescence, and a mentality desiring losing weight is quite noticeable. The number of patients with eating disorders in Japan has increased recently, and it has been found that the number of patients with eating disorders has been increased by about 10 times during 20 years from 1980. The prominent symptoms of anorexia nervosa are lack of food appetite, losing weight, amenorrhea, etc. and the anorexia nervosa is characterized by refusal of maintenance of the minimum standards of body weight. The prominent symptoms of bulimia nervosa are to have a behavior of frequently repeating overeating so-called "eating for diversion", and an inadequate compensatory behavior such as vomiting or abusing laxatives just after overeating. As stated above, these two conditions looks like completely opposite diseases, but a patient with anorexia nervosa may show the symptoms of bulimia nervosa several months later, or on the other hand, a patient with bulimia nervosa often shows the symptoms of anorexia nervosa. Namely, anorexia nervosa and bulimia nervosa are not separate diseases, but diseases which may be shifted each other or overlapped each other, and patients with these conditions are extremely varied, and the disease states are also complicated. The cognitive impairment of body figure and body weight is an essential feature of anorexia nervosa and bulimia nervosa.

For example, serotonin acts on food intake regulation mechanism in the medial hypothalamic area, and particularly inhibits the intake of hydrocarbons. Patients with bulimia nervosa show a potent preference for high-energy food and take significantly increased amount of food at one time, which potently indicate the abnormality of serotonergic neurons. In eating disorders, it is observed that there is a breakdown of the controlling mechanism of eating not only in the brain but also at the peripheral level. Cholecystokinin is a peripheral signal transmitter of satiety, and transmitted into the neutral system via vagus nerve to stop food intake. It is observed in patients suffering from anorexia nervosa that the cholecystokinin overresponds to eating, and on the other hand, in bulimia nervosa, it is assumed that said response to eating disappears. It has also been confirmed in animal tests that the signal of cholecystokinin is transmitted to the central nervous system via serotonergic neurons, and it is pointed out that the transmitting process is possibly disturbed in association with abnormal function of serotonergic neurons.

The patients of anorexia nervosa and bulimia nervosa have various mental and physical disorders in addition to eating disorders. In order to clarify the causes, the dynamics of eating controlling material in cerebrospinal fluid and in blood has been studied. The dynamic change thereof occurs secondarily as a result of eating disorders in most cases and it is a limited case to show such a dynamic change.

For diagnosis of these anorexia nervosa and bulimia nervosa, various studies are reported with using blood or urine samples of the patients, but an established diagnostic method is not yet found. It has been desired to establish a comprehensive therapeutic system for early diagnosis, therapy, social rehabilitation and recurrence prevention in view of the specificity of the diseases. The treatment of eating disorders is done by drug therapy, cognitive behavior therapy, group behavior therapy, and the like. As the drug therapy, there are used antidepressants (cf. Masand P. S. et al., Selective serotonin-reuptake inhibitors; an update., Harvard Rev. Psychiatry (1997) 7: 69-84; and Kaye W. et al., Serotonin neuronal function and selective serotonin reuptake inhibitor treatment in anorexia and bulimia nervosa, Biol. Psychiatry (1998) 44: 825-38).

A brain-derived neurotrophic factor (hereinafter, referred to as "BDNF") is one of neurotrophic factors which has been found in the brain and it is known that it plays an important role for formation and development of brain neural network and further maintenance of survival thereof. In later 1990s, it has been found that BDNF participants in synaptic plasticity and plays also an important role for memory and learning. It is further reported that it has a protecting activity against death of neurocyte. It has been indicated that chronic administration of an antidepressant such as serotonin uptake inhibitors induces increase of BDNF in hippocampus, and therefore it is suggested that there is a correlation between BDNF and serotonergic neurons. It is also suggested by recent study with a transgenic animal that BDNF also participates in eating behavior (cf. Lyons W. E. et al., Brain-derived neurotrophic factor-deficient mice develop aggressiveness and hyperphagia in conjunction with brain serotonergic abnormalities, Proc. Natl. Acad. Sci. USA (1999) 96: 15239-15244). However, there is no report of the role of BDNF in patients suffered from eating disorders.

As mentioned hereinabove, anorexia nervosa and bulimia nervosa have recently increased, but the symptoms thereof are, at a glance, contradictory states of disease and are various and complicated. Accordingly, it is very difficult to diagnose the disorders, which causes further deterioration of the symptoms. Thus, it has been desired in medical field to find improved diagnostic agent, diagnostic method, therapeutic agent and method for detection of therapeutic agent so that the eating disorders can be early diagnosed.

DISCLOSURE OF INVENTION

The present inventors have intensively studies to dissolve the above-mentioned problems and have found that patients suffering from eating disorders have significantly lower blood level of BDNF in comparison with that of healthy persons, and that by utilizing the above difference, the eating disorders can be diagnosed with an antibody against the brain-derived neurotrophic factor (hereinafter, referred to as "anti-BDNF antibody"). The present invention has been accomplished based on this new finding.

That is, the present invention includes the following features.

1. A diagnostic agent for eating disorders comprising as an active ingredient an anti-BDNF antibody.
2. The diagnostic agent for eating disorders as defined in the above 1, for measuring the concentration of BDNF in blood in patients.
3. The diagnostic agent for eating disorders as defined in the above 1 or 2, comprising an anti-BDNF antibody and a labeled anti-BDNF antibody.
4. A diagnostic kit for eating disorders comprising as an active ingredient an anti-BDNF antibody and a labeling agent as the components.
5. The diagnostic kit for eating disorders as defined in the above 4, for measuring the concentration of BDNF in blood in patients.
6. The diagnostic kit for eating disorders as defined in the above 4 or 5, comprising an anti-BDNF antibody and a labeled anti-BDNF antibody.
7. A method for detecting eating disorders which comprises measuring the concentration of BDNF in blood in animals.
8. The method for detecting eating disorders as defined in the above 7, which comprises measuring the concentration of BDNF with an anti-BDNF antibody.
9. The method for detecting eating disorders as defined in the above 7, which comprises measuring the concentration of BDNF with an anti-BDNF antibody and a labeled anti-BDNF antibody.
10. A method for detecting a therapeutic agent of eating disorders, which comprises measuring the concentration of BDNF in blood in animals.
11. A therapeutic agent for eating disorders comprising a compound for increasing BDNF.
12. A therapeutic agent for eating disorders comprising BDNF.

BEST MODE FOR CARRYING OUT THE INVENTION

The diagnostic agent and kit for eating disorders, the method for detecting the eating disorders, the therapeutic agent for the eating disorders, and the method for detecting the therapeutic agent are described in detail below.

The terms in the present description have the following meaning and definition.

The "antibody against brain-derived neurotrophic factor (anti-BDNF antibody)" means an antibody produced by using BDNF as an antigen. Said antibody has an ability to combine to BDNF and includes polyclonal antibodies, monoclonal antibodies. Preferred products are polyclonal antibodies, monoclonal antibodies, etc. which combine specifically to BDNF.

The "labeled antibody against brain-derived neurotrophic factor (labeled anti-BDNF antibody)" means an anti-BDNF antibody labeled with an enzyme (e.g. peroxidase, $\beta$-D-galactosidase, alkali phosphatase, glucose-6-phosphoric dehydrogenase), fluorescent label (e.g. Delfinium), radioisotope or isotope label, or biotin so as to be able to measure the quantity of BDNF. The labeled anti-BDNF antibody includes further an anti-BDNF antibody modified with biotin, 2,4-dinitrophenol, and the like. In the latter case, BDNF can be determined by using a labeled avidin, a labeled anti-2,4-dinitrophenol antibody in addition to the labeled anti-BDNF antibody.

The "eating disorders" mean a heavy disorder in eating behavior including anorexia nervosa and bulimia nervosa, which are observed in many female in puberty/adolescence. The anorexia nervosa is characterized by refusal of maintenance of the minimum standards of body weight, and the bulimia nervosa is characterized by repeating episodes of binge eating and inadequate compensatory behavior associated therewith such as self-induced vomiting, abusing of laxatives, diuretics or other drugs, starvation, excessive exercising. The cognitive deficit of body shape and body weight is essential characteristics of the anorexia nervosa and bulimia nervosa.

The diagnosis of eating disorders by the present invention can be done, for example, in the following manner.

A blood serum is separated from blood of human, and the amount of BDNF in the blood serum is determined by various methods. Preferred method is to determine BDNF by sandwich ELISA using an antibody having high specificity to BDNF. The eating disorders can be diagnosed by utilizing the fact that the concentration of BDNF is significantly lower in the serum of patients suffering from eating disorders in comparison with that of healthy persons.

Specific method of measuring BDNF in blood serum comprises, for example, 1. a step of immobilizing an anti-BDNF antibody onto a solid phase such as polystyrene, nylon, glass, silicone rubber, or sepharose;
2. a step of adding or contacting a blood serum of a patient to be measured to/with the solid phase;
3. a step of washing the solid phase;
4. a step of adding or contacting a labeled anti-BDNF antibody; and
5. a step of measuring the amount of BDNF by utilizing said label.

More specific method of measuring BDNF in blood serum comprises, for example, 1. a step of immobilizing an anti-BDNF antibody onto a solid phase such as polystyrene, nylon, glass, silicone rubber, or sepharose;
2. a step of adding or contacting a blood serum of a patient to be measured to/with the solid phase;
3. a step of washing the solid phase;
4. a step of adding or contacting an anti-BDNF antibody modified with biotin or 2,4-dinitrophenol;
5. a step of adding or contacting a labeled avidin or labeled 2,4-dinitrophenol antibody; and
6. a step of measuring the amount of BDNF by utilizing said label.

A further specific method of measuring BDNF in blood serum comprises, for example, 1. a step of immobilizing an anti-BDNF antibody onto a solid phase such as polystyrene, nylon, glass, silicone rubber, or sepharose;

2. a step of adding or contacting a blood serum of a patient to be measured to/with the solid phase;

3. a step of washing the solid phase;

4. a step of adding or contacting an anti-BDNF antibody modified with biotin;

5. a step of adding or contacting a labeled avidin; and 6. a step of measuring the amount of BDNF by utilizing said label.

The solid phase may be in the form of microspheres, wells, test tube, or the like.

The BDNF to be used as the antigen or a standard for ELISA may be any commercially available product or may be prepared by the following method.

When a genetic engineering technique is used, a gene coding for BDNF is inserted into an appropriate vector, and an appropriate host is transformed with the vector, and the transformed host is cultured, and from the supernatant of the culture, the desired recombinant BDNF is obtained, which is suitable for producing a large amount of homogeneous BDNF product. The host cells to be used in the above are not specifically limited but are inclusive various host cells to have hitherto been used in biotech field, for example, *Escherichia coli*, *Bacillus subtilis*, yeasts, plant cells, or animal cells.

The anti-BDNF antibody can be prepared by immunizing rabbits, chickens, or turkeys by using BDNF as the antigen. The labeled anti-BDNF antibody can be prepared by reacting an anti-BDNF antibody with a commercially available kit of peroxidase with a biotinating agent or a crosslinking agent.

The method of the present invention is also useful for detecting a therapeutic agent for eating disorders. That is, a compound which can increase BDNF will possibly be useful as a therapeutic agent for eating disorders. Further, animal models (e.g. mice, rats) which have lower amount of BDNF are useful as an animal model for eating disorders. Accordingly, a screening of a new therapeutic agent for eating disorders can be effected by utilizing the detecting method of the present invention.

The therapeutic agents to be found by such a method include compounds which can be administered orally or parenterally. The therapeutic agents for eating disorders include BDNF per se and further include thiazole derivatives of the formula:

wherein $R^1$ is a heterocyclic group being optionally substituted, etc., A is a hydroxy group being optionally substituted, etc., B is an aromatic group being optionally substituted, X is oxygen atom, etc., and Y is divalent hydrocarbon group, etc. (cf. JP-A-2001-131161).

The agents also include 5-phenylpyrimidine compounds of the formula;

wherein $R^1$ and $R^2$ are each a halogen atom, $R^3$ and $R^4$ are each a hydrogen atom, an alkyl group having 1 to 5 carbon atoms, an alkylsulfonyl group having 1 to 3 carbon atoms, or an acetylaminoalkyl group, and a salt thereof (cf. JP-A-8-3142).

Other agents are catechol derivatives (cf. Furukawa Y., J. Biol. Chem., vol. 261, p. 6039 (1986); JP-A-63-83020; JP-A-63-156751; JP-A-2-53767; JP-A-2-104568; JP-A-2-149561; JP-A-3-99046; JP-A-3-83921; JP-A-3-86853; JP-A-5-32646), chinone derivatives (cf. JP-A-3-81218; JP-A-4-330010; JP-A-7-285912), glutamic acid derivatives (e.g. JP-A-7-228561), unsaturated fatty acid derivatives (cf. JP-A-8-143454), eudesmane derivatives (cf. JP-A-8-73395), condensed cyclic oxazole derivatives (cf. JP-A-8-175992), carbazole derivatives (cf. JP-A-8-169879), indole derivatives (cf. JP-A-7-118152, JP-A-8-239362), nature-derived terpene derivatives (cf. JP-A-7-149633, JP-A-8-319289), purine derivatives such as Leteprinim (NeuroTherapeutics, USA), and others.

Among those compounds, preferred ones are 2-amino-5-(2,4-dichlorophenyl)pyrimidine (Biochemical Pharmacology 66 (2003) 1019-1023) and 4-(4-chlorophenyl)-2-(2-methyl-1H-imidazol-1-yl)-5-[3-(2-methoxyphenoxy)propyl]-1,3-oxazole (Chem. Pharm. Bull. 51(5) 565-573 (2003)).

The exact dosage and administration schedule of these therapeutic agents for eating disorders may vary depending on required amount, therapeutic method, severity of disease, degree of necessity in each subjects as well as the kinds of agents and hence may be determined by the medical doctors. For instance, in case of BDNF, the dose and times of administration in parental route may vary depending on the conditions, age, body weight of the patients and administration features, but for example, when it is administered by subcutaneous or intravenous injection, the dose is in the range of about 0.1 mg to about 2500 mg per 1 kg of body weight of the patient per day in adult, preferably in the range of about 1 mg to about 500 mg/kg of body weight/day in adult. When it is administered into the trachea in the form of an air spray, the dose is in the range of about 0.1 mg to about 2500 mg per 1 kg of body weight of the patient per day in adult, preferably in the range of about 1 mg to about 500 mg/kg of body weight/day in adult.

The administration schedule may be continuously every day or intermittently done, or in combination thereof. When administered orally, the dose and times of administration may vary depending on the conditions, age, body weight of the patients and administration features, but the dose is, for example, in the range of about 0.5 mg to about 2500 mg per 1 kg of body weight of the patient per day in adult, preferably in the range of about 1 mg to about 1000 mg/kg of body weight/day in adult.

The therapeutic agents for eating disorders obtained by the present invention may be prepared in the form of a pharmaceutical composition by admixture with a pharmaceutically acceptable carrier. The pharmaceutical composition is prepared in the form suitable for parenteral administration (e.g.

subcutaneous injection, muscular injection, or intravenous injection), it is preferable to prepare particularly in the form of a solution or suspension, and for intravaginal or intrarectal administration, it is preferable to prepare particularly in the form of a semi-solid preparation such as a cream or a suppository, and for intranasal administration, it is preferable to prepare particularly in the form of a powder, a nasal drop, or an aerosol preparation.

The pharmaceutical composition may be administered in a single dosage unit form, which is prepared, for example, by any conventional method well known in the pharmaceutical field, for example by the method as described in Remington's Pharmaceutical Science (Mack Publishing Company, Easton, Pa., 1970). For injection preparation, the pharmaceutical carriers include, for example, blood plasma-derived proteins (e.g. albumin), amino acids (e.g. glycine), saccharides (e.g. mannitol). The injection preparation may further include buffer, solubilizing agent, isotonic agent, and the like. In case of using in the form of an aqueous solution preparation or a lyophilized preparation, it is preferable to add a surfactant such as Tween 80 (trademark), Tween 20 (trademark) in order to prevent aggregation. Preparations for parenteral administration other than injection preparation may contain distilled water or physiological saline, polyalkylene glycols (e.g. polyethylene glycol), plant oils, hydrogenated naphthalene, etc. Intravaginal or intrarectal preparations such as suppositories contain as usual carriers, for example, polyalkylene glycol, Vaseline, cacao fats and oils. Intravaginal preparation may contains absorption promoters such as bile salt, ethylenediamine salt, citrate. A preparation for inhalation may be in the form of a solid preparation and may contain, for example, lactose as an excipient. Intranasal drops may be in the form of an aqueous solution or a solution in oil.

EXAMPLES

The present invention is illustrated in more detail by the following examples but should not be construed to be limited thereto.

Example 1

(1) Test subjects:

As is shown in Table I hereinafter, eighteen female patients with bulimia nervosa (BN) (average age 21.6 years old [standard deviation (SD) 4.0], range 16-34 years) and 12 female patients with anorexia nervosa (AN) (average age 19.6 years old [SD 5.9], range 14-34 years) were recruited as test subjects, and age matched healthy subjects (average age 21.6 years old [SD 1.7], range 20-25 years) also participated in this study as normal controls. All patients with AN or BN were diagnosed according to the Diagnostic and Statistical Manual of Mental Disorders IV: DSM-IV (American Medical Association), and the patients with AN were classified in two subtypes; the Restricting Type (n=7), and the Binge-Eating/Purging Type (n=5). All subjects completed the Bulimic Investigatory Test, Edinburgh (BITE) and the 17-item Hamilton Depression Rating Scale (HDRS) (cf. Br. J. Soc. Clin. Psychol. 6: 278-296 (1967)). The BITE is a 33-item self-report questionnaire, which is designed as an objective screening test for use in a wide variety of settings to identify subjects with symptoms of bulimia or binge-eating/purging type symptoms. Threshold scores for clinical significance are symptom score of 20 or more (cf. Henderson et al., (1987), A self-rating scale for bulimia. The "BITE", Bri. J. Psychiatry 150: 18-24). The 17-item HDRS were used to measure depressive symptomatology. Body weight and height and the body mass index (BMI: $kg/m^2$) were measured. The duration of illness in the patients with AN and BN was 1.8 years [SD 1.7] and 3.8 years [SD 2.5] in average, respectively. Antipsychotic drugs administered for treatment were risperidone (4 mg/day; n=1), fluvoxamine (50-150 mg/day; n=4), paroxetine (20 mg/day; n=1), trazodone (25 mg/day; n=1) in the patients with BN, and paroxetine (20-30 mg/day; n=2), risperidone (1 mg/day; n=1) in the patients with AN. Of the patients, twenty patients were drug naive.

(2) Test Method:

Serum samples of the test subjects were collected and stored at −80° C. until assay. Serum levels of BDNF were measured by using the BDNF assay kit (Promega, USA) according to the manufacturer's instructions. Briefly, 96-well plates were coated with anti-BDNF monoclonal antibody and incubated at 4° C. for 18 hours. The plates were incubated in a blocking buffer at room temperature for one hour. After washing with buffer, diluted serum (100 μL) was added thereto. BDNF standards containing human BDNF (78-5000 pg/mL) were used. The plates were incubated at room temperature for 2 hours, followed by washing with a washing buffer five times, and incubated with anti-IgY antibody conjugated to horseradish peroxidase at room temperature for one hour. After washing with a buffer five times, TMB solution (100 μL) was added thereto, and incubated at room temperature for ten minutes. Reaction was stopped with 1M hydrochloric acid (100 μL) and the absorbance at 450 nm was measured with an automated microplate reader (Emax, Molecular Devices, USA) within 30 minutes. The amount of BDNF in the test samples was measured by sandwich ELISA assay, and the concentration of BDNF was calculated based on the calibration curve.

(3) Statistical Analysis

The data were presented as the mean±standard deviation (SD). The differences among three groups were examined by means of one-way layout dispersion analysis (analysis of variance: ANOVA). Bonferroni/Dunn test was adopted for multiple comparisons among treatment means. Statistical analysis of two groups was performed using Student's t-test. Relationships between variables were ascertained by means of Pearson's product moment correlation coefficients. The p values <0.05 were considered statistically significant.

(4) Results

The characteristics of the test subjects and the above test results are shown in Table I.

TABLE 1

|  | NC (N = 21) | AN (N = 12) | BN (N = 18) | p |
| --- | --- | --- | --- | --- |
| Age (years) | 21.3 (1.71) | 19.6 (5.89) | 21.6 (3.97) | NS |
| Duration of illness (years) |  | 1.76 (1.33) | 3.72 (2.36) | 0.013* |
| Body weight (kg) | 50.8 (4.60) | 38.1 (4.55) | 50.4 (4.96) | <0.0001*+ |
| BMI ($kg/m^2$) | 20.0 (1.54) | 15.3 (1.84) | 20.4 (2.09) | <0.0001*+ |

TABLE 1-continued

| | NC (N = 21) | AN (N = 12) | BN (N = 18) | p |
|---|---|---|---|---|
| BDNF (µg/ml) | 61.4 (19.5) | 24.9 (6.75) | 38.4 (15.3) | <0.027*, <0.0001†, <0.0001†† |
| BITE symptom scale | 5.86 (5.94) | 17.3 (7.45) | 23.8 (2.73) | 0.003*, <0.0001†, <0.0001†† |
| BITE severity scale | 1.90 (3.77) | 7.08 (5.55) | 12.3 (6.49) | 0.011*, <0.0093†, <0.0001†† |
| 17-Item HDRS | 7.67 (6.14) | 18.3 (6.11) | 19.4 (6.03) | <0.0001†, <0.0001†† |

Figure 1:
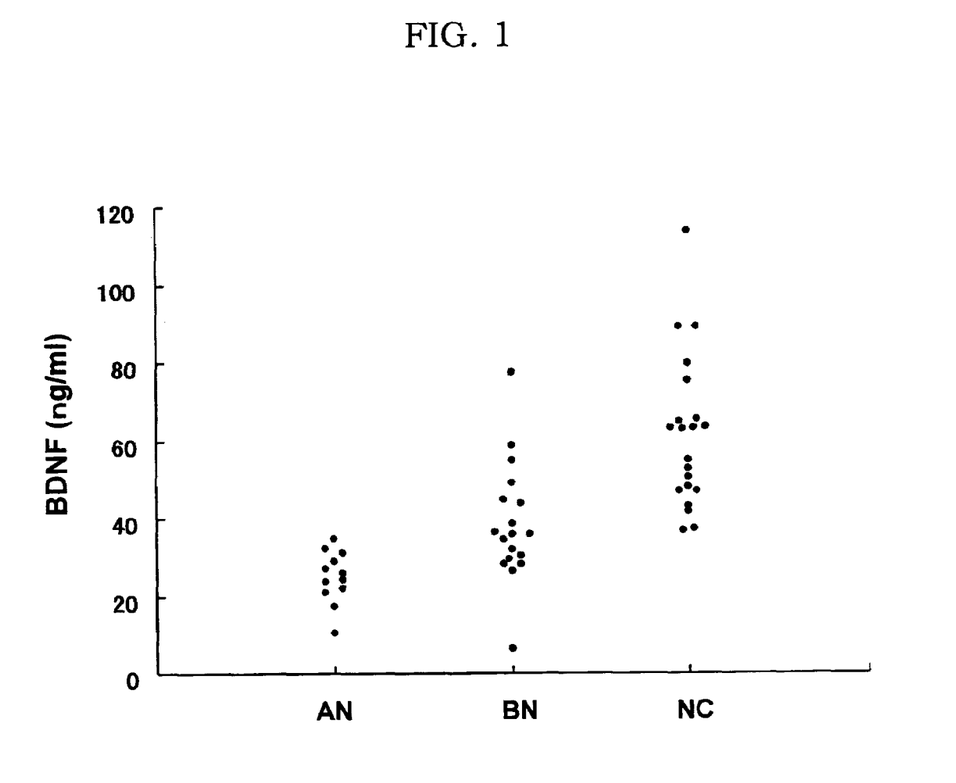
FIG. 1 is a scatter spot of BDNF concentration in blood serum in normal control (NC), and patients with bulimia nervosa (BN) and anorexia nervosa (AN).

NC = Normal controls;
AN = anorexia nervosa;
BN = bulimia nervosa
BMI = Body mass index;
BDNF = Brain-derived neurotrophic factor;
BITE = The bulimic investigatory test, Edinburgh;
17-Item HDRS = 17-Item Hamilton depression rating scale
The values are the mean (SD).
NS = Not significant
p* = Comparisons between AN and BN;
p† = Comparisons between AN and NC;
p†† = Comparisons between BN and NC i) Serum BDNF Concentration in All Test Subjects Scatter plot of the serum BDNF concentration in the normal controls (CN) and in the patients with bulimia nervosa (BN) and anorexia nervosa (AN) is shown in FIG. 1.

One-way ANOVA showed significant differences among three groups (F=22.33 [2,48], p<0.0001), and Bonferroni/Dunn tests showed that serum levels (mean 61.4 ng/ml [SD 19.5]) of BDNF in the normal controls were significantly higher than those in the patients with BN (mean 38.4 ng/ml [SD 15.3], p<0.0001) or the patients with AN (mean 24.9 ng/ml [SD 6.75], p<0.0001). Serum levels of BDNF in the patients with BN were significantly (p=0.027) greater than those in the patients with AN. No age difference in the three groups was detected (Table I). Serum levels of BDNF in the patients with the binge-eating/purging type (n=5) of AN (mean 27.82 ng/ml [SD 6.76]) were not significantly different from those of the restricting type (n=7) of AN (mean 22.83 ng/ml [SD 6.39]) (Student's t-test, p=0.222). In the all groups combined (n=51), there was no significant correlation (r=0.079, p=0.585) between serum BDNF levels and age. In the all patients (n=30), there was no significant correlation (r=0.04, p=0.836) between serum BDNF levels and the duration of illness.

ii) Serum BDNF and Serum BMI

Figure 2:
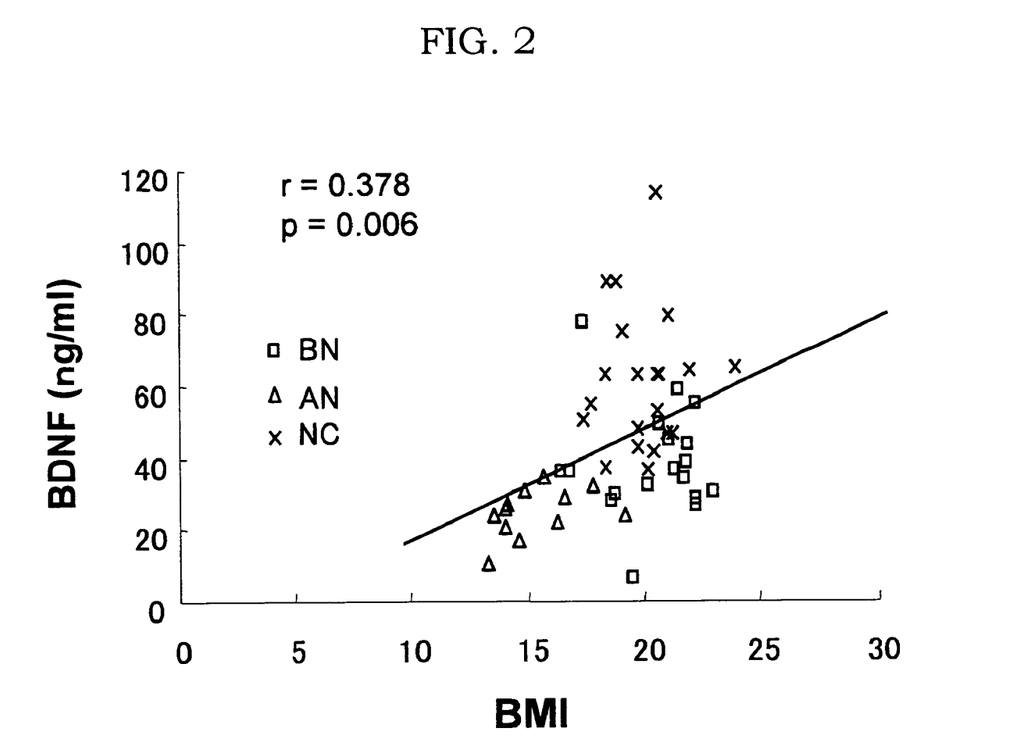
FIG. 2 is a graph showing correlation between serum BDNF level and serum BMI level in all test subjects.

Correlation between serum levels of BDNF and serum levels of BMI in all test subjects is shown in FIG. 2.

One-way ANOVA showed significant differences among three groups (F=32.76 [2,48], p<0.0001), and Bonferroni/Dunn tests showed that the values (mean 20.01 kg/m² [SD 1.54]) of BMI in the normal controls were significantly higher than those in the patients with AN (mean 15.33 kg/m² [SD 1.84]), whereas no significant difference between normal controls and the patients with BN (mean 20.36 kg/m² [SD 2.09]) was detected. In the all groups combined (n=51), there was a significant positive correlation (r=0.378, p=0.006) between serum BDNF levels and BMI (cf. FIG. 2). Furthermore, a significant positive correlation (r=0.396, p=0.030) between serum BDNF levels and BMI was also observed in the all patients (n=30). However, in the all groups combined (n=51), there was no significant correlation (r=−0.044, p=0.761) between BMI and age. Thus, it was found that the serum BDNF levels in drug naïve patients were not different from those of medicated patients both in AN (Student's t-test, p=0.222) and BN (Student's t-test, p=0.230).

iii) Comparisons Between Serum BDNF Levels and Clinical Rating Scales iii-1) BITE and 17-Items HDRS As is shown in Table I as to the BITE and 17-item HDRS scores in the three groups, one-way ANOVA showed significant differences among three groups (F=53.30 [2,48], p<0.0001), and Bonferroni/Dunn tests showed that the values (mean 5.86 [SD 5.94]) of BITE in the normal controls were significantly (p<0.0001) lower than those in the patients with AN (mean 17.25 [SD 7.45]) or BN (mean 23.78 [SD 2.73]). The BITE score of patients with BN was significantly (p=0.003) greater than those of patients with AN. In the all groups combined (n=51), there was no significant correlation (r=−0.078, p=0.585) between BITE scores and age.

Figure 4:
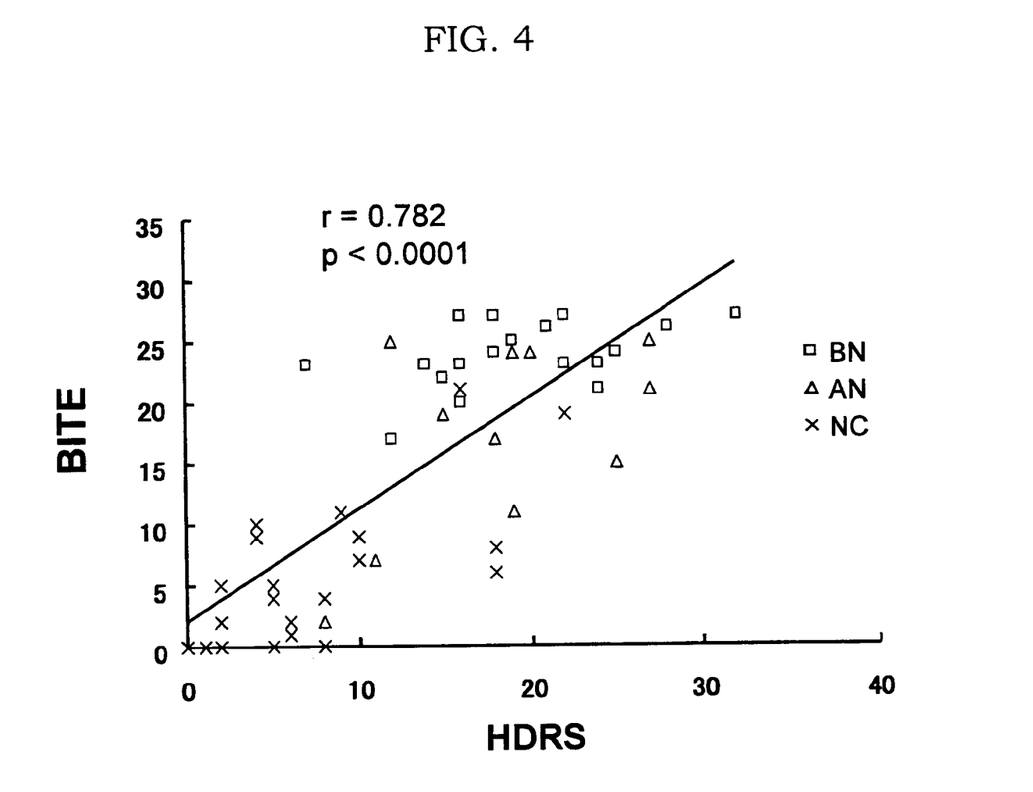
FIG. 4 is a graph showing correlation between HDRS score and BITE score in all subjects.

Further, the correlation between BITE scores and HDRS in all test subjects is shown in FIG. 4. As is shown in FIG. 4, there was significant positive correlation (r=0.782, p=0.0001) between them.

iii-2) Serum BDNF and 17-Items HDRS Scores

Figure 3:
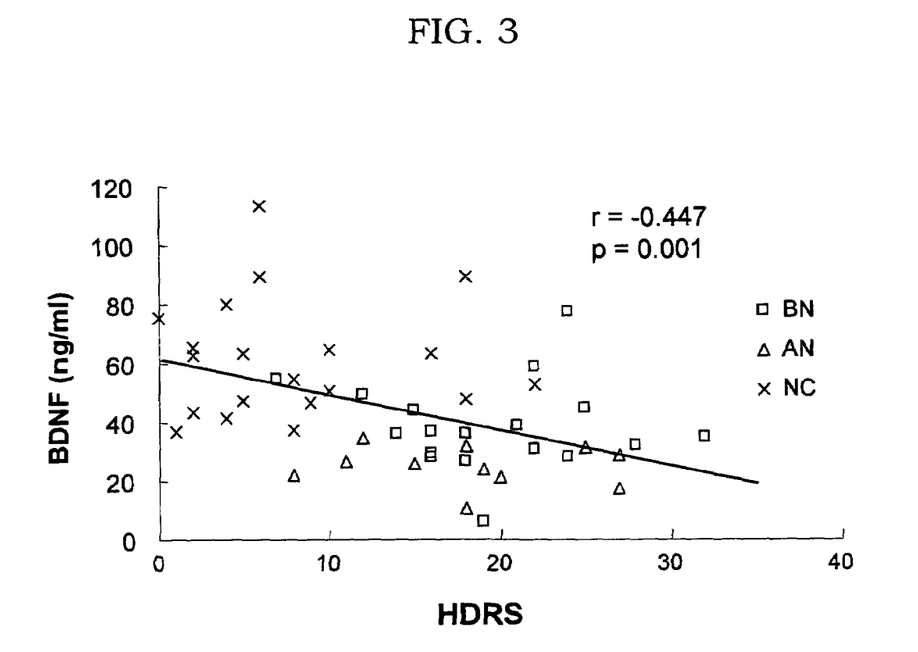
FIG. 3 is a graph showing correlation between serum BDNF level and HDRS score in all test subjects.

Correlation between serum levels of BDNF and HDRS scores in all test subjects is shown in FIG. 3. In the all groups combined (n=51), there was significant negative correlation (r=−0.447, p=0.001) between HDRS scores and serum BDNF levels.

One-way ANOVA showed significant differences among three groups (F=21.23 [2,48], p<0.0001), and Bonferroni/Dunn tests showed that the values (mean 7.67 [SD 6.14]) of 17-item HDRS in the normal controls were significantly (p<0.0001) higher than those in the patients with AN (mean 18.25 [SD 6.11]) or BN (mean 19.39 [SD 6.03]).

As is seen from the above test results, serum BDNF levels of female patients with eating disorders (AN and BN) are significantly decreased as compared with those of age-matched female normal controls, and serum BDNF levels in the patient with AN are significantly lower than those in the patients with BN. It is also clear that serum BDNF levels are inversely correlated with HDRS scores and the measurement of depressive symptoms. In the all test subjects, there was a significant correlation between serum BDNF levels and BMI values. However, serum BDNF levels of the patients with BN, who had normal BMI values, were significantly lower than those of normal controls, which suggests that lowered serum BDNF levels are not due to decreased BMI values. Taken together, it is likely that reduced serum BDNF levels might contribute to pathophysiology of eating disorders.

The primary behavioral abnormality in eating disorders is dysfunction in regulation of food intake, such as restriction, binge-eating and purging. The patients with eating disorders in the above tests had the abnormal behaviors represented by their BMI values and BITE scores. In the above tests, with respect to the relation of the BDNF levels to the BMI and BITE, there were differences between BN and AN, which was unexpected from the animal study. Consequently, it is possible that lowered BDNF levels may be associated with binge-eating and purging behaviors and maintenance function in weight regulation of eating disorders. On the other hand, they are likely to be anxious and hyperactive when body weight is increasing. Therefore, it is likely that loss of body weight is not a cause rather a consequence of abnormal eating behaviors associated with lowered BDNF levels.

In summary, it will be understood that BDNF plays a very important role in the pathophysiology of eating disorders (AN and BN) and that BDNF in blood may be useful as a biological marker for eating disorders.

Example 2

There were used male BDNF (+/−)heterozygous mice (20 week old) which were purchased from Jackson, USA and were self-replicated in Chiba University. A recombinant human BDNF (40 mg/kg, dissolved in 0.3 ml physiological saline) was administered to one mouse, and a physiological saline (0.3 ml) was administered to another mouse, wherein both were administered by subcutaneous injection once a day for 5 days. The amounts of feed taken by the mice for 24 hours were measured by a devise for measuring feeding in mice (Merquest, Toyama, Japan). The results are shown in FIG. 5.

Figure 5:
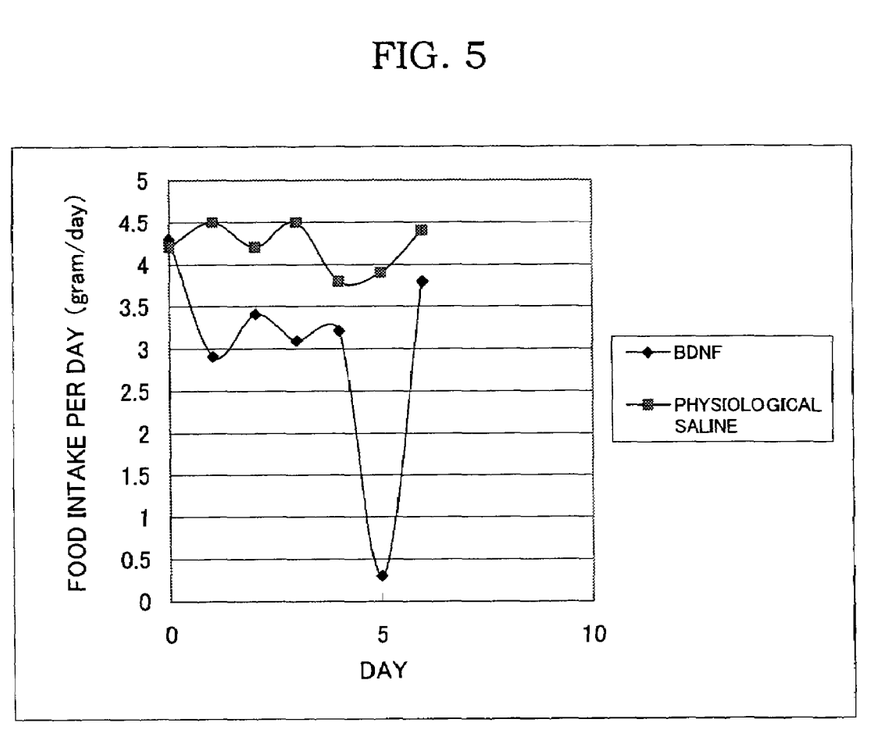
FIG. 5 is a graph comparing the amounts of feed taken per day between the mice injected with BDNF and the mice injected with a physiological saline.

As is shown in FIG. 5, when BDNF was administered to the BDNF (+/−)heterozygous mouse wherein the amount of BDNF was about 50% of that in wild type mouse, the food intake per day was decreased in comparison with that in the mouse administered with physiological saline.

It is clear from the test result that the abnormal food intake of the BDNF (+/−)heterozygous mouse was decreased by administering BDNF. That is, it is indicated that the behavioral abnormality in eating is improved by administration of BDNF. Thus, it is understood that the abnormal food intake (binge-eating, etc.) in the patients with eating disorders will be inhibited by administering a drug such as BDNF, BDNF derivatives or any drug having an activity of increasing BDNF, and thereby the eating disorders will be remedied. Moreover, a new therapeutic method for eating disorders will be expected by applying a BDNF gene therapy.

INDUSTRIAL APPLICABILITY

The present invention provides a diagnostic agent for eating disorders comprising as an active ingredient anti-BDNF antibody, which is useful for diagnosis of eating disorders by measuring BDNF in blood with the antibody. Particularly, diagnosis of eating disorders can be easily done by measuring the concentration of BDNF in blood of the patients by using an anti-BDNF antibody and a labeled anti-BDNF antibody.

The invention claimed is:

1. A method for detecting one or more eating disorders selected from the group consisting of anorexia nervosa and bulimia nervosa which comprises measuring the concentration of brain-derived neurotrophic factor (BDNF) in blood in a human subject, wherein a decreased concentration of BDNF in the blood of said subject compared to the BDNF level in a normal control subject is indicative of anorexia nervosa or bulimia nervosa.

2. The method according to claim 1, which comprises measuring the concentration of brain-derived neurotrophic factor (BDNF) with an antibody against brain-derived neurotrophic factor.

3. The method according to claim 1, which comprises measuring the concentration of brain-derived neurotrophic factor (BDNF) with an antibody directed against brain-derived neurotrophic factor and a labeled antibody directed against brain-derived neurotrophic factor.

4. A method for detecting one or more eating disorders selected from the group consisting of anorexia nervosa and bulimia nervosa comprising:
    detecting the concentration of brain-derived neurotrophic factor (BDNF) in the blood or serum of a human subject, wherein a lower level of BDNF in the blood or serum of said subject compared to that in the blood or serum of a normal control subject is indicative of anorexia nervosa or bulimia nervosa.

5. The method of claim 4, wherein said subject is a female.

6. The method of claim 4, wherein said subject is a pubescent or adolescent female.

7. The method of claim 4, wherein said disorder is anorexia nervosa.

8. The method of claim 4, wherein said disorder is bulimia nervosa.

9. The method of claim 4, which uses a sandwich ELISA and a BDNF specific antibody to detect BDNF levels.

* * * * *